United States Patent [19]

Lavagnino et al.

[11] 4,282,170

[45] Aug. 4, 1981

[54] 9-CARBAMOYL-9-(2-CYANOETHYL)FLUORENES

[75] Inventors: Edward R. Lavagnino; Andrew J. Pike; Jack B. Campbell, all of Indianapolis, Ind.

[73] Assignee: Eli Lilly and Company, Indianapolis, Ind.

[21] Appl. No.: 141,229

[22] Filed: Apr. 17, 1980

[51] Int. Cl.³ ............................................. C07C 121/78
[52] U.S. Cl. ................................. 260/465 D; 424/324; 564/164
[58] Field of Search ...................................... 260/465 D

[56] References Cited

U.S. PATENT DOCUMENTS

| 3,325,544 | 6/1967 | Moffett | 260/570.8 |
| 3,660,485 | 5/1972 | Cusic et al. | 260/558 H |
| 3,843,657 | 10/1974 | Lowrie | 260/558 A X |

FOREIGN PATENT DOCUMENTS 960758  6/1964  United Kingdom .

*Primary Examiner*—Dolph H. Torrence
*Attorney, Agent, or Firm*—Joseph A. Jones; Arthur R. Whale

[57] ABSTRACT

9-Carbamoyl-9-(2-cyanoethyl)fluorenes are intermediates for synthesis of 9-aminoalkyl-9-carbamoyl-fluorenes, which are antiarrhythmic agents.

6 Claims, No Drawings

9-CARBAMOYL-9-(2-CYANOETHYL)FLUORENES

BACKGROUND OF THE INVENTION

1. Field of the Invention

This invention provides a group of 9-carbamoyl-9-(2-cyanoethyl)fluorenes which are important intermediates in the synthesis of 9-aminoalkyl-9-carbamoylfluorenes, which compounds are useful antiarrhythmic agents.

2. State of the Art

Fluorene cheistry has long been studied, and many articles and patents discuss various 9-substituted fluorenes. For example, U.S. Pat. No. 3,325,544, of Moffett, makes 9-hydroxy-9-(1-amino-2-propyl)fluorenes by way of a 9-(1-cyanoethyl)-9-hydroxyfluorene intermediate. U.S. Pat. No. 3,660,485, of Cusic et al., discloses 9-aminoalkyl-9-hydrazinocarbonylfluorenes. U.S. Pat. No. 3,843,657, of Lowrie, discloses 9-aminoalkyl-9-(alkylaminoalkylcarbamoyl)fluorenes.

SUMMARY OF THE INVENTION

This invention provides intermediate compounds of the formula

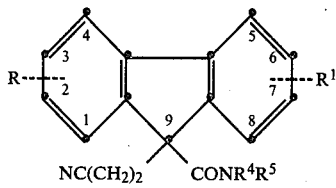

wherein R and $R^1$ independently are hydrogen, $C_1$-$C_4$ alkyl, fluoro or chloro; $R^4$ and $R^5$ independently are hydrogen or $C_1$-$C_6$ alkyl.

Description of the Preferred Embodiments

In this document, all temperatures will be measured in degrees Celsius.

The terms $C_1$-$C_4$ and $C_1$-$C_6$ alkyl refer to groups such as methyl, ethyl, propyl, isopropyl, butyl, s-butyl, i-butyl, t-butyl, pentyl, neopentyl, hexyl, 1,1-dimethylbutyl and the like.

The compounds of this invention are made by the reaction of the corresponding 9-carbamoylfluorene with acrylonitrile in the presence of a base, preferably a cationic base. The 9-carbamoylfluorenes are well known in organic chemical literature. The reactions are carried out at moderate temperatures and are complete in economically brief reaction times.

The preferred bases in which the reaction is carried out are the basic quaternary ammonium hydroxide salts, of which the most preferred example is benzyltrimethylammonium hydroxide, which is sold by Rohm and Haas Corporation under the trademark Triton B. Other related bases are also highly preferred; such bases include tetraethylammonium hydroxide, phenyltrimethylammonium hydroxide, methyltributylammonium hydroxide and the like. Only a catalytic amount of a quaternary ammonium hydroxide base is needed, such as from about 0.01 mole to about 0.5 mole per mole of compound to be produced.

Bases other than the quaternary ammonium compounds are also useful, such as the inorganic bases such as the hydroxides, carbonates and bicarbonates of sodium, potassium and lithium, the alkali metal alkoxides such as lithium butoxide and sodium methoxide, the alkyllithiums such as butyllithium and ethyllithium, and the hydrides such as sodium hydride and potassium hydride. Bases such as the above are used in amounts equimolar with the reactants, or in slight excess amounts.

The reaction is carried out in an inert orgnic solvent. The choice of solvent is not critical and any desired solvent may be chosen from among such classes of solvents as the ethers, the alkanes, the halogenated hydrocarbons, the esters, the amides, and the ketones. More specifically, suitable solvents include among many others, dioxane, tetrahydrofuran, diethyl ether, ethyl acetate, hexane, chlorobenzene, the di- and trichlorobenzenes, bromomethane, acetone, methyl isobutyl ketone, dimethylformamide, dimethylacetamide, ethanol, butanol, and the like.

The reaction is effectively carried out at temperatures in the range from about 0° to about 100°. It is often advantageous to operate at the boiling point of the reaction mixture, under reflux. It is preferred to carry out the reaction at moderately elevated temperatures in the range of from about ambient temperature to about 75°, and more highly preferred to operate at from about 35° to about 75°.

It is not necessary to use substantial excess quantities of either reactant. As is the custom in organic chemistry, a small excess of the less expensive reactant, usually the acrylonitrile, may be used to assure that the more expensive reactant is fully consumed. For this purpose, small excess amounts in the range of 1 to 10 percent are used. The use of large excess amounts, even up to 100 percent excess or more, is not harmful to the process and such excess amounts may be used if desired; however, large excesses are not necessary.

The order of addition of the reactants in this process is not important. It is quite satisfactory simply to combine both reactants and the base in the solvent, and to heat the reaction mixture to the desired temperature. Reaction times in the range of from about 1 to about 12 hours achieve essentially complete reaction. In some cases, shorter reaction times are acceptable, especially when temperatures at the hotter part of the temperature range are used.

A preferred reaction technique is to combine the reactants in stoichiometric amounts with the base and heat the reaction mixture at about 50° for a few hours. Then some excess acrylonitrile and additional base are added, and the mixture is held for several hours or overnight at about 50° with stirring.

It is believed that the compounds of this invention are clearly understandable from the above generic formula. To assure that the reader fully understands the compounds, however, the following group of representatives are mentioned.

9-carbamoyl-9-(2-cyanoethyl)-4-methylfluorene
9-carbamoyl-9-(2-cyanoethyl)-3-ethylfluorene
9-carbamoyl-9-(2-cyanoethyl)-2-propylfluorene
1-(t-butyl)-9-carbamoyl-9-(2-cyanoethyl)fluorene
9-carbamoyl-9-(2-cyanoethyl)-2-ethyl-6-propylfluorene
1-(i-butyl)-9-carbamoyl-9-(2-cyanoethyl)fluorene
9-carbamoyl-9-(2-cyanoethyl)-1,5-dimethylfluorene
9-carbamoyl-9-(2-cyanoethyl)-3-fluoro-7-propylfluorene
9-carbamoyl-9-(2-cyanoethyl)-2-fluorofluorene
9-carbamoyl-4,5-dichloro-9-(2-cyanoethyl)fluorene
9-carbamoyl-2,6-dichloro-9-(2-cyanoethyl)fluorene
9-carbamoyl-3-chloro-9-(2-cyanoethyl)-6-ethylfluorene 2-fluoro-5-(s-butyl)-9-carbamoyl-9-(2-cyanoethyl)fluorene
9-(2-cyanoethyl)-9-(N-ethylcarbamoyl)-4-propylfluorene
9-(2-cyanoethyl)-9-(N,N-dipropylcarbamoyl)fluorene
9-(N-butyl-N-ethylcarbamoyl)-9-(2-cyanoethyl)-3-methylfluorene
9-(2-cyanoethyl)-9-(N-hexylcarbamoyl)-2-isopropylfluorene A preferred group of compounds of this invention includes the compounds of the formula above wherein R and $R^1$ are hydrogen. Another preferred group of compounds includes those wherein $R^4$ and $R^5$ are hydrogen. The most preferred compound of this invention is the compound wherein all of R, $R^1$, $R^4$ and $R^5$ are hydrogen.

The following examples are provided to assure that the reader can prepare any desired compound of this invention.

EXAMPLE 1

9-Carbamoyl-9-(2-cyanoethyl)fluorene

A 4.2 g. portion of 9-carbamoylfluorene was dissolved in 300 ml. of dioxane at 45° C. To the solution was added 0.4 ml. of Triton B (40% benzyltrimethylammonium hydroxide in methanol) and 1.1 g. of acrylonitrile. The reaction mixture was stirred at 70° C. for one hour and was then allowed to cool to ambient temperature and stand overnight. The dioxane was removed under vacuum, and the remaining oil was taken up in ethyl acetate/water. The layers were separated, and the organic layer was washed three times with water and once with saturated sodium chloride solution. The organic layer was then dried over magnesium sulfate, filtered and evaporated under vacuum to a foam, which was taken up in dichloromethane. The solution was boiled, and hexane was added until crystallization occurred. The mixture was chilled overnight, and the crystals were collected by filtration. The crystals were washed with hexane and dried under vacuum at 40° to obtain 3.2 g. of the desired product, m.p. 148°–152°, with sintering at 143°.

The product was subjected to infrared analysis in chloroform, showing a nitrile band at 2260 cm$^{-1}$, amide proton bands at 3400 and 3520 cm$^{-1}$, and the carbonyl band at 1690 cm$^{-1}$. Sixty mHz nuclear magnetic resonance analysis in CDCl$_3$ using a tetramethylsilane reference showed triplets (2H) centered about $\delta$1.6 and $\delta$2.8, indicating the protons on the methylene groups.

EXAMPLE 2

9-Carbamoyl-9-(2-cyanoethyl)fluorene

One hundred g. of 9-carbamoylfluorene was slurried in 3375 ml. of tetrahydrofuran in a 5-liter flask. The mixture was heated to 45° with stirring, and to it was added 10 ml. of Triton B. The mixture was stirred for 15 minutes at constant temperature, and 26.2 g. of acrylonitrile was then added in one portion. The mixture was stirred at the reflux temperature for 3 hours, and was then allowed to cool to room temperature. The mixture was then concentrated under vacuum to a solid, which was purified as described in Example 1 above to obtain 110 g. of product, analytically identical to the product of Example 1.

EXAMPLE 3

9-Carbamoyl-9-(2-cyanoethyl)fluorene

Five hundred g. of 9-carbamoylfluorene was slurried in 13 liters of tetrahydrofuran under nitrogen, and the mixture was stirred and heated to 50°. Fifty ml. of Triton B was added, followed by 131 g. of acrylonitrile. The mixture was stirred at 50° for 6 hours, and 65 g. of additional acrylonitrile and 25 ml. of Triton B were added. The mixture was stirred at 50° overnight.

The reaction mixture was then cooled and filtered through a filter aid pad, and the filtrate was evaporated to a solid under vacuum. The solid was dissolved in ethyl acetate/water, the layers were separated, and the product was isolated from the organic layer as described in Example 1. The crude product was recrystallized from methanol to provide 433 g. of purified product identical to the material obtained in Example 1.

EXAMPLE 4

9-(2-cyanoethyl)-9-(N,N-dimethylcarbamoyl)fluorene

A 28 g. of portion of 9-(N,N-dimethylcarbamoyl)fluorene was added to a 3-liter flask, and 1 liter of tetrahydrofuran was added. The mixture was heated to 45°, and 10 ml. of Triton B was added. The mixture was stirred at constant temperature for 15 minutes, and then 8 g. of acrylonitrile was added in one portion. The mixture was then stirred at reflux temperature for 3 hours, and was cooled and concentrated under vacuum to obtain 51.8 g. of oil. The product was isolated as described in Example 1 and was recrystallized from hexane to obtain 15 g. of first-crop purified product, m.p. 109°–110°. Infrared analysis showed a characteristic carbonyl band at 1610 cm$^{-1}$, and a characteristic nitrile band at 2220 cm$^{-1}$.

EXAMPLE 5

9-(2-cyanoethyl)-9-(N-methylcarbamoyl)fluorene

A 36.8 g. portion of 9-(N-methylcarbamoyl)fluorene was reacted with 10.6 g. of acrylonitrile in the presence of 10 g. of Triton B in tetrahydrofuran as described in Example 4. The reaction mixture was then concentrated under vacuum to a semi-solid, which was added to ice-water/ethyl acetate. The organic layer was separated, washed with water, and dried over sodium sulfate. The solution was evaporated to dryness to obtain 45.8 g. of crude product, which was crystallized from ethyl acetate/hexane to obtain 30 g. of the desired product, m.p. 185°–187°. Infrared analysis of the product showed a carbonyl band at 1685 cm$^{-1}$ and a nitrile band at 2270 cm$^{-1}$.

The compounds of this invention are used as intermediates for the synthesis of an important series of antiarrhythmic agents of the formula

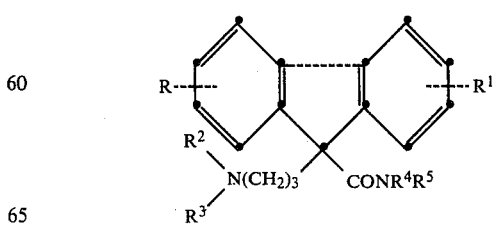

wherein R, $R^1$, $R^4$ and $R^5$ are as defined above, and $R^2$ and $R^3$ independently are hydrogen, $C_1$–$C_6$ alkyl, CH$_2$(C$_2$-C$_5$ alkenyl), phenyl (C$_1$-C$_3$ alkyl), or taken together with the nitrogen to which they are attached are a cyclic group of the formula

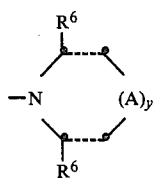

wherein R$^6$ is hydrogen or C$_1$-C$_4$ alkyl; A is —CH$_2$—, oxygen or nitrogen; and y is zero or one; and the pharmaceutically acceptable salts thereof.

The antiarrhythmics described above are prepared from the compounds of this invention by reduction in the presence of an amine having the R$^2$ and R$^3$ substituents, or by reduction of the nitrile group to a primary amine, followed by introduction of the R$^2$ and R$^3$ groups.

The one-step process will be described first. This process is effective for all the antiarrhythmic compounds except those where R$^2$ or R$^3$ is alkenyl. The process is carried out by hydrogenating a compound of this invention in the presence of an amine of the formula R$^2$R$^3$NH where R$^2$ and R$^3$ have the special definition just given.

It should be pointed out that chlorine atoms on the phenyl rings of the compound of this invention (the R and R$^1$ groups) are relatively susceptible to being hydrogenated off the molecule. Thus, compounds having such atoms must be hydrogenated under mild conditions, at relatively low temperatures and relatively low hydrogen pressures, and preferably in an acidic reaction mixture, especially a mixture containing the appropriate hydrohalide. Thus, it is preferable to prepare antiarrhythmic compounds having such R and R$^1$ groups by the two-step process, since that process is more adaptable to operation under acid conditions than is the one-step process.

The one-step reduction-amination is carried out at hydrogen pressures from about 2 atmospheres to about 150 atmospheres, and at temperatures from about the ambient temperature to about 100°. The usual hydrogenation catalysts are effective. Platinum, palladium, nickel, rhodium and ruthenium catalysts may be used as desired. Platinum oxide is a preferred catalyst at relatively low temperatures and pressures, and carbon-supported palladium is a preferred catalyst at relatively high temperatures and pressures. Organic solvents may be used in the reaction mixture, but it is preferred to carry out the reaction neat, using a sufficient excess of the amine to provide a stirrable liquid mixture. If desired, ethers, alcohols, aromatics, and amides may be used as solvents, however.

In both the one-step and two-step processes, amounts of hydrogenation catalyst in the range from about 1% to about 25%, based on the weight of the starting compound, may be used. The amount of catalyst is not critical; it is usually preferred to use amounts in the range from about 5% to about 20%.

The two-step synthesis of the antiarrhythmic products is carried out by first hydrogenating the compound of this invention to convert the cyanoethyl group to an aminopropyl group, and then alkylating the amino group to provide the desired R$^2$ and R$^3$ substituents. The two-step process is useful to prepare all of the antiarrhythmic compounds, except those where R$^2$ and R$^3$ form a cyclic structure. The hydrogenation step is carried out substantially as described above, except that it is advisable to operate at relatively mild conditions, such as at temperatures from about the ambient temperature to about 70°, and at hydrogen pressures from about 2 to about 4 atmospheres. It is also advisable to operate in an acidic medium, most preferably in glacial acetic acid. Organic solvents as described above may be used, but it is preferred to use no solvent except the acetic acid.

A preferred technique for preparing compounds wherein R$^2$ is hydrogen and R$^3$ is alkyl or phenylalkyl is to combine the 9-(3-aminopropyl) compound with the appropriate aldehyde or ketone to prepare the Schiff base, and to hydrogenate the Schiff base at relatively mild conditions, such as with palladium catalyst at from about one to about 4 atmospheres at moderate temperatures from about ambient temperature to about 50° to prepare the desired product.

Alkylaminopropyl compounds may also be prepared by alkylating a 9-(3-aminopropyl)fluorene by standard means to provide the R$^2$ and R$^3$ substituents. The alkylation reactions are carried out by combining the alkylating agent in the presence of a base, such as those described above in the description of the synthesis of compounds of this invention, or a tertiary amine such as pyridine or triethylamine, in an inert organic solvent. Alkylating agents include halides, such as bromides or chlorides formed with the desired R$^2$ or R$^3$ group, and are of the formula R$^2$X and R$^3$X, where X is halogen, preferably chloro or bromo. Typical such alkylating agents are allyl bromide, benzyl bromide, 1-bromobutane and the like. Solvents for this step include the same classes described above in the discussion of synthesis of compounds of this invention. It will be understood that, where R$^2$ and R$^3$ are different and neither is hydrogen, alkylations may be carried out successively to place first one and then the other of the R$^2$ and R$^3$ substituents.

The following preparations are shown to illustrate reactions of compounds of this invention to prepare the final antiarrhythmic products.

Preparation 1

A 6.56 g. portion of 9-carbamoyl-9-(2-cyanoethyl)-fluorene was combined with 75 ml. of isopropylamine and hydrogenated in the presence of 2 g. of platinum oxide at 4 atmospheres and 60° for 16 hours. The reaction took up 0.05 mole of molecular hydrogen, the theoretical amount.

The reaction mixture was then filtered and evaporated under vacuum to a solid. The solid was taken up in tetrahydrofuran and evaporated to a solid three times to remove the residual isopropylamine. The remaining solid was dissolved in ethyl acetate and was extracted twice with 1 N hydrochloric acid. The acid extracts were combined, washed with ethyl acetate, and then covered with additional ethyl acetate. The mixture was made basic with 50% sodium hydroxide solution, whereupon the product came out of the aqueous layer and dissolved in the ethyl acetate layer. The basic layer was separated and extracted twice more with additional ethyl acetate. The combined organic layers were washed with water and with saturated sodium chloride solution, dried for 16 hours with sodium sulfate, filtered and evaporated under vacuum to a solid, 9-carbamoyl-9-(3-isopropylaminopropyl)fluorene, m.p. 94°–95°. The solid was dissolved in methanol, filtered and treated with anhydrous hydrogen chloride. The solution was evaporated to a solid under vacuum, which solid was then taken up in methanol and evaporated twice to remove as much hydrogen chloride as possible. The solid was then crystallized from 10 ml. of hot chloroform. The crystals were filtered, washed with cold chloroform and dried under vacuum at 60° to obtain 2.1 g. of 9-carbamoyl-9-(3-isopropylaminopropyl)fluorene, hydrochloride, m.p. 216.5°–217°.

Preparation 2

A 500 g. portion of 9-carbamoyl-9-(2-cyanoethyl)fluorene, 1400 ml. of isopropylamine and 100 g. of 5% palladium/carbon catalyst were placed in a 4-liter high pressure hydrogenation apparatus, which was pressurized with hydrogen at 100 atmospheres. The reaction mixture was stirred and heated at 100° for 10 hours, and was then allowed to cool. The reaction mixture was then rinsed out of the reactor with tetrahydrofuran, and the mixture was filtered. The filtrate was evaporated to dryness, and the product was isolated and converted to the hydrochloride as described in Preparation 1 to obtain 391 g. of 9-carbamoyl-9-(3-isopropylaminopropyl)fluorene, hydrochloride, identical to the product of Preparation 1.

Preparation 3

A 3.3 g. portion of 9-carbamoyl-9-(2-cyanoethyl)fluorene was hydrogenated in 95 ml. of glacial acetic acid at 4 atmospheres and ambient temperature for 2 hours in the presence of 1.5 g. of platinum oxide catalyst. The theoretical amount of hydrogen (0.025 mole) was taken up. The acetic acid was then removed under vacuum, and the residue was layered in ethyl acetate/1 N hydrochloric acid. The aqueous layer was separated and washed with ethyl acetate, and the acidic solution was made basic with 50% sodium hydroxide and extracted twice with ethyl acetate. The combined organic layers were washed with water and with saturated sodium chloride solution, dried over sodium sulfate, filtered and evaporated under vacuum to obtain 2.3 g. of white solid. Its melting point was 146°–149° dec. The solid was analyzed by nuclear magnetic resonance technique on a 60 mHz instrument in $CDCl_3$ using tetramethylsilane as reference. The amine protons were indicated by a broad singlet (2H) at $\delta 1.0$, replaceable with $D_2O$.

The solid above, 9-(3-aminopropyl)-9-carbamoylfluorene, was taken up in 1 N hydrochloric acid, filtered and diluted with water to 100 ml. The solution was then lyophilized, and the solid was crystallized by dissolving it in 50 ml. of methanol, and boiling off the methanol, replacing it with ethyl acetate to maintain constant volume. The solids were separated by filtration and dried under vacuum at 60° to obtain 1 g. of 9-(3-aminopropyl)-9-carbamoylfluorene, hydrochloride, m.p. 198°–200° C.

Preparation 4

A 13 g. portion of 9-(2-cyanoethyl)-9-(N,N-dimethylcarbamoyl)fluorene was hydrogenated in the presence of 115 ml. of isopropylamine and 3 g. of 5% palladium/carbon catalyst at 100 atmospheres pressure and 100° for 10 hours. The reaction mixture was then washed out of the reactor with tetrahydrofuran, and was filtered and concentrated under vacuum to obtain 17 g. of oil, which was dissolved in diethyl ether and poured into ice-water. The ether layer was washed with water, and extracted 3 times with 6 N hydrochloric acid. The acid extracts were combined and made basic with 10% sodium hydroxide solution, and the oily precipitate by extracted into diethyl ether. The ether extract was washed 3 times with water, dried over anhydrous sodium sulfate, and concentrated under vacuum to obtain 16.8 g. of oil, which was dissolved in dry diethyl ether. Hydrogen chloride gas was bubbled into the ether solution. The white precipitate which formed was separated by filtration and dried in a vacuum oven. The dry solid was recrystallized from ethanol/diethyl ether to obtain 8.9 g. of 9-(3-isopropylaminopropyl)-9-(N,N-dimethylcarbamoyl)fluorene, hydrochloride, m.p. 170°–171° dec. The product was subjected to nuclear magnetic resonance analysis on a 60 mHz instrument in $CDCl_3$, using tetramethylsilane as a reference standard. The spectrum showed two closely spaced singlets at $\delta 7.5$, and an aromatic multiplet at $\delta 7.8$. The methyl groups of the isopropyl group were visible as singlets at $\delta 1.2$ and 1.3.

Preparation 5

A 6.7 g. portion of 9-(3-aminopropyl)-9-carbamoylfluorene was dissolved in 90 ml. of ethanol, 1.6 g. of acetone was added, and the mixture was stirred overnight at 40°. Two g. of 5% palladium/carbon was added, and the mixture was hydrogenated for 2 hours at ambient temperature under 4 atmospheres pressure. The uptake of hydrogen was 0.05 mole, the theoretical amount. The reaction mixture was then filtered, and the filtrate was concentrated under vacuum to a foam. The foam was dissolved in ethyl acetate and extracted twice with 1 N hydrochloric acid. The combined aqueous extracts were washed twice with ethyl acetate and then covered with additional ethyl acetate. With stirring, the mixture was made basic with 50% sodium hydroxide solution. The layers were then separated, and the aqueous layer was extracted again with ethyl acetate. The combined organic layers were washed twice with water and once with saturated sodium chloride solution, dried over sodium sulfate, filtered and evaporated under vacuum to yield 3 g. of 9-carbamoyl-9-(3-isopropylaminopropyl)fluorene, identical to the intermediate product of Preparation 1.

Preparation 6

A 24 g. portion of 9-(N-methylcarbamoyl)-9-(2-cyanoethyl)fluorene was added to 230 ml. of isopropylamine and was hydrogenated at 100 atmospheres pressure and 100° for 10 hours in the presence of 5 g. of 5% palladium/carbon catalyst. The reaction mixture was then filtered and concentrated to obtain 36.4 g. of an oil, which was dissolved in diethyl ether and added to ice-water. The organic layer was washed with water and extracted three times with 6 N hydrochloric acid. The acid layers were combined and made basic with 10% sodium hydroxide and the white precipitate was extracted into diethyl ether. The ether extract was washed with water, dried over sodium sulfate and concentrated to yield 23 g. of crude 9-(3-isopropylaminopropyl)-9-(N-methylcarbamoyl)fluorene.

The 9-aminoalkylfluorenes are useful as antiarrhythmic agents. Such utility has been determined by evaluating representative compounds in biological assays designed to measure antiarrhythmic activity. One such assay comprises administering a compound to a dog suffering from an experimentally induced cardiac arrhythmia, and observing whether or not the compound effects a conversion of the arrhythmia to normal sinus rhythm, and if so, for how long the conversion persists.

In a typical experiment to determine the activity of the compounds, one or more mongrel dogs of either sex were anesthetized with sodium pentobarbital. A 23 gauge Butterfly infusion needle was placed in the radial vein for the introduction into the dog of sufficient ouabain to induce an arrhythmia, and for the introduction into the dog of the test compound. Each dog was continuously monitored throughout the experiment by electrocardiogram. After the ouabain induced cardiac arrhythmia had continued for thirty minutes, a compound was administered via the Butterfly infusion needle at the rate of 200 μg per kilogram of dog body weight per minute. If the arrhythmia was not converted to a normal sinus rhythm within ten minutes from the initial administration of test compound, as observed by electrocardiogram, the rate of infusion of test compound was increased to 500 μg per kilogram per minute. The amount of test compound required to convert an arrhythmia to normal rhythm was recorded as the "converting dose". Following the complete administration of test compound to the dog, the dog's heart was monitored by electrocardiogram until such time that an arrhythmia returned to the dog's heart, or for a maximum time of two hours, at which time the experiment was terminated. The duration of normal rhythm was recorded in minutes.

The results of several experiments are set out in the following table. Most of the compounds were evaluated more than once, as indicated in the "No. of Dogs" column. The average converting dose is given in mg. per kilogram of animal body weight. Average duration of conversion is recorded in minutes.

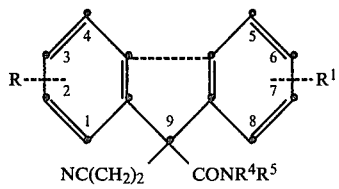

| $R^1$ | $R^2$ | $R^3$ | No. of dogs | Converting dose mg/kg | Duration minutes |
|---|---|---|---|---|---|
| $CONH_2$ | H | i-Pr | 3 | 0.7 | 120 |
| $CONH_2$ | $CH_3$ | $CH_3$ | 1 | 3.2 | 80 |

In another biological assay, known in the art as the canine HIS bundle electrogram, the effects of antiarrhythmic agents on conduction intervals and refractory periods in various regions of the heart are determined. When 9-(3-isopropylaminopropyl)-9-carbamoylfluorene, hydrochloride, was compared to the antiarrhythmic agent aprindine in the canine HIS bundle electrogram, it proved to be at least twice as potent in prolonging conduction intervals and refractory periods.

The compounds can be employed in combatting cardiac arrhythmias in animals by administering an antiarrhythmic amount of one or more of the aminoalkylfluorenes to an animal. The compounds are effective as antiarrhythmic agents when administered internally to an animal so as to introduce the compound into the animal's cardiovascular system.

We claim:

1. A compound of the formula wherein R and $R^1$ independently are hydrogen, $C_1$–$C_4$ alkyl, fluoro or chloro; $R^4$ and $R^5$ independently are hydrogen or $C_1$–$C_6$ alkyl.

2. A compound of claim 1 wherein R and $R^1$ are hydrogen.

3. A compound of claim 1 wherein $R^4$ and $R^5$ are hydrogen.

4. The compound of claim 1 wherein R, $R^1$, $R^4$ and $R^5$ are hydrogen.

5. The compound of claim 1 wherein R and $R^1$ are hydrogen and $R^4$ and $R^5$ are methyl.

6. The compound of claim 1 wherein R, $R^1$ and $R^4$ are hydrogen and $R^5$ is methyl.

* * * * *